(12) United States Patent
Pandey (10) Patent No.: US 8,845,657 B2
(45) Date of Patent: Sep. 30, 2014

(54) SURGICAL SUPPORT ASSEMBLY (75) Inventor: Ashwini K. Pandey, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 102 days.

(21) Appl. No.: 13/437,142

(22) Filed: Apr. 2, 2012

(65) Prior Publication Data
US 2012/0303050 A1  Nov. 29, 2012

Related U.S. Application Data (60) Provisional application No. 61/489,441, filed on May 24, 2011.

(51) Int. Cl.
| A61B 19/00 | (2006.01) |
| A61B 1/313 | (2006.01) |
| A61B 17/00 | (2006.01) |
| A61B 17/29 | (2006.01) |

(52) U.S. Cl.
CPC ........... *A61B 17/00234* (2013.01); *A61B 1/313* (2013.01); *A61B 2017/2927* (2013.01); *A61B 19/26* (2013.01)
USPC ....................................................... 606/130

(58) Field of Classification Search
USPC .............. 606/1, 108, 130; 600/102, 112–114, 600/141–142, 184, 201, 204, 210, 211, 600/214–219, 225–235, 245
See application file for complete search history.

(56) References Cited

U.S. PATENT DOCUMENTS

| 1,706,500 | A | * | 3/1929 | Smith | 600/232 |
|---|---|---|---|---|---|
| 3,299,883 | A | | 1/1967 | Rubens | |
| 3,534,729 | A | | 10/1970 | Sakamoto | |
| 3,724,449 | A | * | 4/1973 | Gauthier | 600/215 |
| 4,156,424 | A | * | 5/1979 | Burgin | 600/213 |
| 4,573,452 | A | * | 3/1986 | Greenberg | 600/102 |
| 5,183,033 | A | | 2/1993 | Wilk | |
| 5,603,689 | A | * | 2/1997 | Lucini | 600/201 |
| 5,688,243 | A | | 11/1997 | Rammler | |
| 5,749,362 | A | | 5/1998 | Funda et al. | |
| 5,797,835 | A | | 8/1998 | Green | |
| 6,530,930 | B1 | | 3/2003 | Marino et al. | |
| 6,589,254 | B2 | * | 7/2003 | Fontenot | 606/130 |
| 6,966,876 | B2 | * | 11/2005 | Irion et al. | 600/102 |
| 8,118,736 | B2 | * | 2/2012 | Zook et al. | 600/184 |
| 8,512,353 | B2 | * | 8/2013 | Rosielle | 606/130 |

(Continued)

FOREIGN PATENT DOCUMENTS

| EP | 246086 A2 * 11/1987 ............. A61B 17/02 |

OTHER PUBLICATIONS

Australian Examination Report dated Jun. 5, 2013 issued in Australian Application No. 2012202304.

*Primary Examiner* — David Eastwood (57) ABSTRACT

A surgical support apparatus is disclosed, including an elongate member, a first tissue penetrating member, and a second tissue penetrating member. The second tissue penetrating member includes two segments hingably attached to each other. A distal portion of the second segment of the second tissue penetrating member includes an engagement surface. The first tissue penetrating member has a distal portion including a receiving surface. The engagement surface radially approaches the receiving surface causing the secure engagement of the first and second tissue penetrating members. Surgical objects can be attached to the surgical support apparatus and supported within an internal body cavity. Also disclosed is a method of assembling the surgical support apparatus in an internal body cavity.

16 Claims, 7 Drawing Sheets

(56) References Cited

U.S. PATENT DOCUMENTS

| | | | |
|---|---|---|---|
| 2001/0002429 A1* | 5/2001 | Hu et al. | 600/210 |
| 2001/0020121 A1* | 9/2001 | Hu et al. | 600/232 |
| 2001/0041827 A1* | 11/2001 | Spence et al. | 600/201 |
| 2004/0059192 A1* | 3/2004 | Cartier et al. | 600/210 |
| 2004/0186353 A1* | 9/2004 | Palermo | 600/201 |
| 2006/0122580 A1 | 6/2006 | Dannan | |
| 2006/0253109 A1* | 11/2006 | Chu | 606/1 |
| 2006/0270902 A1* | 11/2006 | Igarashi et al. | 600/114 |
| 2008/0091066 A1 | 4/2008 | Sholev | |
| 2011/0009706 A1* | 1/2011 | Abdelgany et al. | 600/233 |
| 2011/0133040 A1* | 6/2011 | Viola et al. | 248/68.1 |
| 2011/0288376 A1* | 11/2011 | Tepper | 600/210 |

* cited by examiner

SURGICAL SUPPORT ASSEMBLY

CROSS REFERENCE TO RELATED APPLICATION

The present application claims the benefit of and priority to U.S. Provisional Application Ser. No. 61/489,441, filed on May 24, 2011, the entire contents of which are incorporated herein by reference.

BACKGROUND

1. Technical Field

This application generally relates to the field of minimally invasive procedures. More particularly, the present disclosure relates to a surgical support apparatus for positioning and securing surgical objects within a body cavity.

2. Background of Related Art

Today, many surgical procedures are performed through small incisions in the skin, as compared to the larger incisions typically required in traditional procedures, in an effort to reduce both trauma to the patient and recovery time. Generally, such procedures are referred to as endoscopic, unless performed on the patient's abdomen, in which case the procedure is referred to as laparoscopic. Throughout the present disclosure, the term "minimally invasive" should be understood to encompass both endoscopic and laparoscopic procedures. During a typical minimally invasive procedure, surgical objects, such as surgical access ports (e.g., trocar and/or cannula assemblies), endoscopes, or other instruments, are inserted into the patient's body through the incision in tissue. Prior to the introduction of the surgical object into the patient's body, insufflation gases may be used to enlarge the area surrounding the target surgical site to create a larger, more accessible work area.

The nature of minimally invasive surgery requires that the number and size of incisions into tissue be kept to a minimum. Creating separate incisions for separate surgical objects is problematic, as is creating larger incisions through which multiple instruments can be inserted simultaneously.

Certain minimally invasive procedures require that a number of surgical instruments to be inserted into a body cavity at a given time. However, some surgical objects need to be present in a body cavity, but do not need to be under direct operator control at all times. Thus, a need arises for a device that can securely maintain surgical objects within a body cavity, while allowing an operator to manipulate other surgical objects during a minimally invasive procedure.

SUMMARY

The present disclosure is directed toward a support apparatus for maintaining surgical objects in a body cavity.

The surgical support apparatus includes a platform disposed above a body surface. The platform may be attached to an arm or clamp extending from another structure, such as a surgical table or support arm. In embodiments, the platform may be separate from any external support and will rest upon a body surface. The platform generally has a flat, planar profile, but may be curved or otherwise shaped. The platform may be rigid, resilient, or malleable.

Extending from a distal surface of the platform is a first tissue penetrating member which has a substantially straight profile. A second tissue penetrating member also extends from the platform and has a first segment and a second segment, the second segment located distally of the first segment. The first and second tissue penetrating members may be needles, or may have any suitable shape or profile to penetrate tissue and maintain a substantially straight condition while inserted into tissue.

At or near a distal end of the second segment of the second tissue penetrating member is an engagement surface, which may be a pointed distal end, or may be defined by protruding surface features such as knurls, ridges or grooves. The first tissue penetrating member has a receiving surface in a distal portion for receiving the engagement surface. The receiving surface may be a notch, groove, divot, or other suitable textured surface.

The first and second segments of the second tissue penetrating member are hingably attached such that the second segment is free to rotate about the point of attachment to the first segment. The second tissue penetrating member may incorporate a locking mechanism to keep the first and second segments disposed in a substantially straight condition for insertion into tissue.

The second tissue penetrating member may include an actuation member to control the rotation of the second segment with respect to the first segment. The actuation member may be a tensile element such as a cable, string, or suture, or may be a rigid element such as a bar, rod, or lever through which an operator may exert tensile or compressive forces on the second segment.

The first and second tissue penetrating members may be fixably attached to the platform, or in embodiments, may be free to pivot relative the platform. Accordingly, the first and/or second tissue penetrating members may incorporate a lock to fix the first and second tissue penetrating members in a desired orientation relative to the platform.

In use, an operator will insert the first tissue and second tissue penetrating members into a layer of tissue either sequentially or simultaneously. The operator will then rotate the second segment of the second tissue penetrating member towards the receiving surface of the first tissue penetrating member. The first and second tissue penetrating members may be disposed on the platform such that when contact is made between the engagement surface and the receiving surface, a compressive force is generated. This compressive force ensures that the engagement surface and the receiving surface securely engage either by friction or interference. With the first and second tissue securely engaged, surgical objects can be introduced to the body cavity and attached to the first or second tissue penetrating members.

These and other embodiments of the present disclosure will be described in greater detail below with reference to the appended figures.

BRIEF DESCRIPTION OF THE DRAWINGS

The accompanying drawings, which are incorporated in and form part of the specification, illustrate the present disclosure when viewed with reference to the description, wherein.

Other features of the present disclosure will become apparent from the following detailed description taken in conjunction with the accompanying drawings, which illustrate, by way of example, the principles of the present disclosure.

DETAILED DESCRIPTION OF EMBODIMENTS

The present disclosure will now describe in detail embodiments of a surgical support apparatus with reference to the drawings in which like reference numerals designate identical or substantially similar parts in each view. Throughout the description, the term "proximal" will refer to the portion of the assembly closest to the operator, whereas the term "distal" will refer to the portion of the assembly farthest from the operator.

It will be understood that various modifications may be made to the embodiments disclosed herein. Therefore, the above description should not be construed as limiting, but merely as exemplifications of embodiments. Those skilled in the art will envision other modifications within the scope and spirit of the present disclosure.

Figure 1:
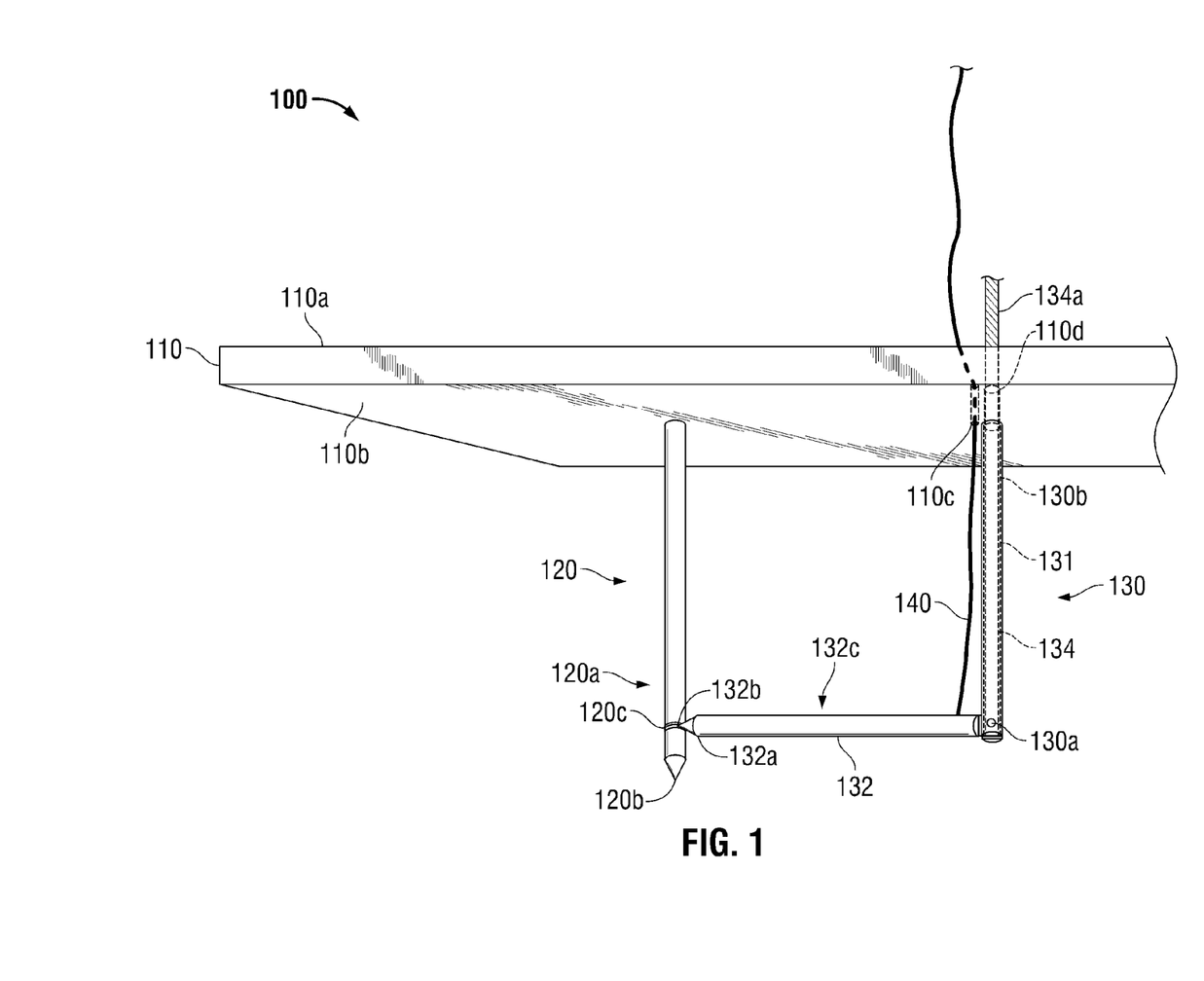
FIG. 1 is a perspective view of a surgical support apparatus, fully assembled, having a platform, a first tissue penetrating member, a second tissue penetrating member, a locking mechanism, and an actuation member.
Figure 2:
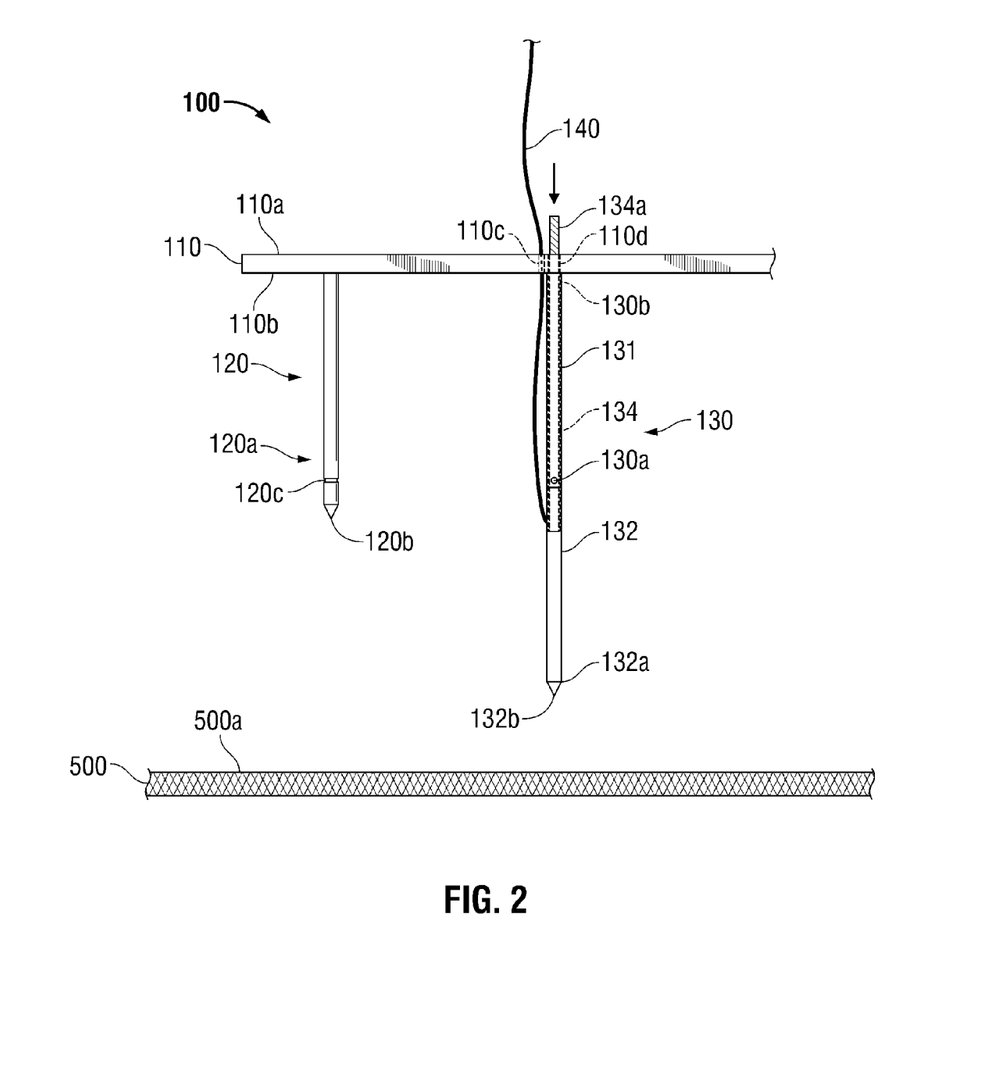
FIG. 2 is a side profile view of the surgical support apparatus as shown in FIG. 1, prior to insertion through a layer of tissue.

Referring initially to FIG. 1, a surgical support apparatus 100 is shown. The surgical support apparatus 100 includes a platform 110 that is disposed over a body surface 500a (FIG. 2). Platform 110 may be attached to a surgical table, support arm, or other external member (not shown). Platform 110 has a proximal surface 110a and a distal surface 110b, and has a substantially planar profile. Other shaped or curved profiles are contemplated for platform 110. Platform 110 is formed of a material suitable for prolonged contact with a layer of tissue 500 (FIG. 2). Such materials may be metal, plastic, composites, or polymers. Platform 110 may be rigid, resilient, or sufficiently malleable to contour to a shaped body surface or other geometry.

Extending from a portion of distal end 110b of platform 110 is a tissue penetrating member 120. Tissue penetrating member 120 is fixably attached to the distal surface 110b of platform 110 by any suitable method, such as adhesion, welding, press fit, or coupling with a nail, tack, or screw. Tissue penetrating member 120 may be disposed substantially perpendicular to platform 110 or may be disposed at another desired angle with respect to platform 110. Tissue penetrating member 120 has a substantially straight configuration suitable for insertion into a layer of tissue 500. Tissue penetrating member 120 has a distal portion 120a and a distal end 120b. In the distal portion 120a of tissue penetrating member 120 is a receiving surface 120c for engaging other components of the surgical articulation apparatus, as will be discussed further below.

Tissue penetrating member 120 may be a needle, as shown here, or may have any number of other shapes and cross-sectional profiles suitable for insertion into layer of tissue 500. Tissue penetrating member 120 may be formed of metal, polymer, or any other suitable material. The distal end 120b of tissue penetrating member 120 may be pointed as shown to cut through tissue, or may be blunted, to be inserted through a pre-cut incision in tissue.

Tissue penetrating member 130 extends from a portion of distal surface 110b of platform 110 and is laterally spaced from tissue penetrating member 120. Tissue penetrating member 130 may be shaped or formed in a substantially similar manner to tissue penetrating member 120. Tissue penetrating member 130 includes two segments 131, 132. First segment 131 is fixably attached to the platform 110 in a manner similar to tissue penetrating member 120 discussed above. As with tissue penetrating member 120, tissue penetrating member 130 may be disposed substantially perpendicular to the distal surface 110b of platform 110, or may be disposed at another desired angle. Second segment 132 is located distally of first segment 131, and is hingably attached to the first segment 131 at a point of attachment 130a. Similar to tissue penetrating member 120, tissue penetrating member 130 may have a pointed or blunted tip.

First and second segments 131, 132 may be hingably attached with a pin-and-collar configuration as shown, or any other suitable attachment such as a ball-and-socket configuration or cable and sleeve arrangement. Second segment 132 is rotatable about the point of attachment 130a relative to first segment 131. Second segment 132 may be rotatable in a single plane, or may be free to rotate in multiple planes.

Prior to insertion through tissue, second segment 132 is locked in a substantially straight condition with respect to first segment 131 for insertion into a layer of tissue 500. Locking first segment 131 and second segment 132 may be accomplished with a sliding tab 134 as shown.

Sliding tab 134 (shown in phantom) is an elongate member that is disposed within a passage 130b of tissue penetrating member 130 and extends proximally through an aperture 110d in platform 110 to be engaged by an operator. Aperture 110d may align with the passage 130b through the tissue penetrating member 130. Sliding tab 134 may frictionally engage the passage 130b such that the frictional engagement of sliding tab 134 and passage 130b inhibits sliding tab 134 from translating through passage 130b without being forced by an operator. Sliding tab 134 may have an arcuate profile, may be hollow, solid, or otherwise shaped or configured. Sliding tab 134 has a proximal portion 134a which may be grasped by an operator, and may include a handle or grip. Sliding tab 134 translates through passage 130b to a portion of second segment 132 such that sliding tab 134 interferes with the rotation of second segment 132. Accordingly, the sliding tab 134 is configured to accommodate the configuration of the point of attachment 130a of the first and second segments 131, 132 so that the sliding tab 134 may translate distally into the second segment 132. To unlock second segment 132, proximal portion 134a of sliding tab 134 is engaged by an operator and the sliding tab 134 is translated proximally such that second segment 132 is free to rotate about point of attachment 130a.

In embodiments, a sliding tab may be embedded within a portion of a tissue penetrating member, or may be configured as a sleeve disposed on an outer surface of tissue penetrating member 130 to bind second segment 132 within the inner circumference of the sleeve.

Disposed on a distal end 132a of the second segment 132 is an engagement surface 132b for securely engaging the receiving surface 120c. In embodiments, the engagement surface 132b may be located on a distal portion 132c of the second tissue penetrating member 132. Engagement surface 132b may be a ledge, groove, knurled or frictional surface, or may be a pointed edge as shown. Engagement surface 132b is configured such that when placed in contact with the receiving surface 120c, the engagement surface 132b contacts the receiving member 120c such that the second segment 132 is maintained in its radial position with respect to segment 131.

Engagement surface 132b and receiving surface 120c are brought into contact when the second segment 132 of tissue penetrating member 130 is rotated about the point of attachment 130a in the direction of tissue penetrating member 120. Sliding tab 134 will be translated proximally of the point of attachment 130a of the second segment 131 to the second segment 132 so that the second segment 132 may rotate freely about the point of attachment 130a. An operator may rotate second segment 132 with an instrument such as graspers or forceps, or with an actuation member 140, as will be discussed further below. Secure contact between the engagement surface 132b and the receiving surface 120c may be effected by the compression of tissue penetrating members 120, 130 due to their relative proximity on the platform 110. Accordingly, tissue penetrating members 120, 130 may be spaced along the distal surface 110b of platform 110 such that a compressive force is generated when the engagement surface 132b contacts the receiving surface 120c. The tissue penetrating members 120, 130 may be sufficiently resilient to undergo elastic deformation in the course of the fixation of engagement surface 132b and receiving surface 120c. Where the engagement surface 132b and receiving surface 120c are configured to frictionally engage, the compression of the tissue penetrating members 120, 130 provides the necessary force to maintain the contact of the engagement surface 132b and the receiving surface 120c. Where the engagement surface 132b and receiving surface 120c engage by interference, the compression of the tissue penetrating members 120, 130 ensures the continuous engagement of interfering surface geometries or protrusions.

The engagement of tissue penetrating members 120, 130 is sufficient such that disengagement of the tissue penetrating members 120, 130 may only be effected by the intervention of an operator. Accordingly, forces exerted on tissue penetrating members 120, 130 incidental to minimally invasive surgery will not disengage tissue penetrating members 120, 130.

An actuation member 140 may be attached to a portion of the second segment 132 and extend from the second segment 132 proximally through the layer of tissue 500 and platform 110. Actuation member 140 may be a tensile element such as a cable, wire, or suture. Platform 110 may include an aperture 110c through which actuation member 140 may pass. An operator can thus grasp a portion of the actuation member 140 and exert a tensile force to effect rotation of the second segment 132 about the point of attachment 130a. Accordingly, an operator controls the degree to which the second segment 132 rotates about the point of attachment 130a from an area proximal of the platform 110. In this way, the operator also controls the secure coupling of the engagement surface 132b and receiving surface 120c. In embodiments, the actuation member 140 may be configured as a rigid member such as a bar, rod, or lever through which an operator can exert compressive or tensile forces to effect rotation of the second segment 132 about the point of attachment 130a.

Actuation member 140 may also be used to disengage engagement surface 132b and receiving surface 120c. As the actuation member 140 is pulled further proximally by an operator, the compressive forces that hold engagement surface 132b and receiving surface 120c together may be overcome by the tensile forces exerted by the tensile member 140. Aperture 110c may be dimensioned such that an operator may pull actuation member 140 in a manner to offset second segment 132 from a radial path that aligns with tissue penetrating member 120, allowing second segment 132 to fall freely or in a controlled manner to a substantially straight condition with first segment 131. Alternatively, sliding tab 134 may be used to exert a distal force on second segment 132 to overcome the compressive forces holding engagement surface 132b and receiving surface 120c in secure relation.

Turning to FIG. 2, the surgical support apparatus 100 is shown disposed above a layer of tissue 500 with the tissue penetrating members 120, 130 disengaged from each other and prior to insertion into a layer of tissue 500. Tissue penetrating members 120, 130 are substantially straight, easing insertion into the layer of tissue 500. Accordingly, sliding tab 134 (shown in phantom) is shown translated distally within passage 130b, maintaining second segment 132 in a substantially straight condition with respect to segment 131 and inhibiting rotation about the point of attachment 130a.

Figure 3:
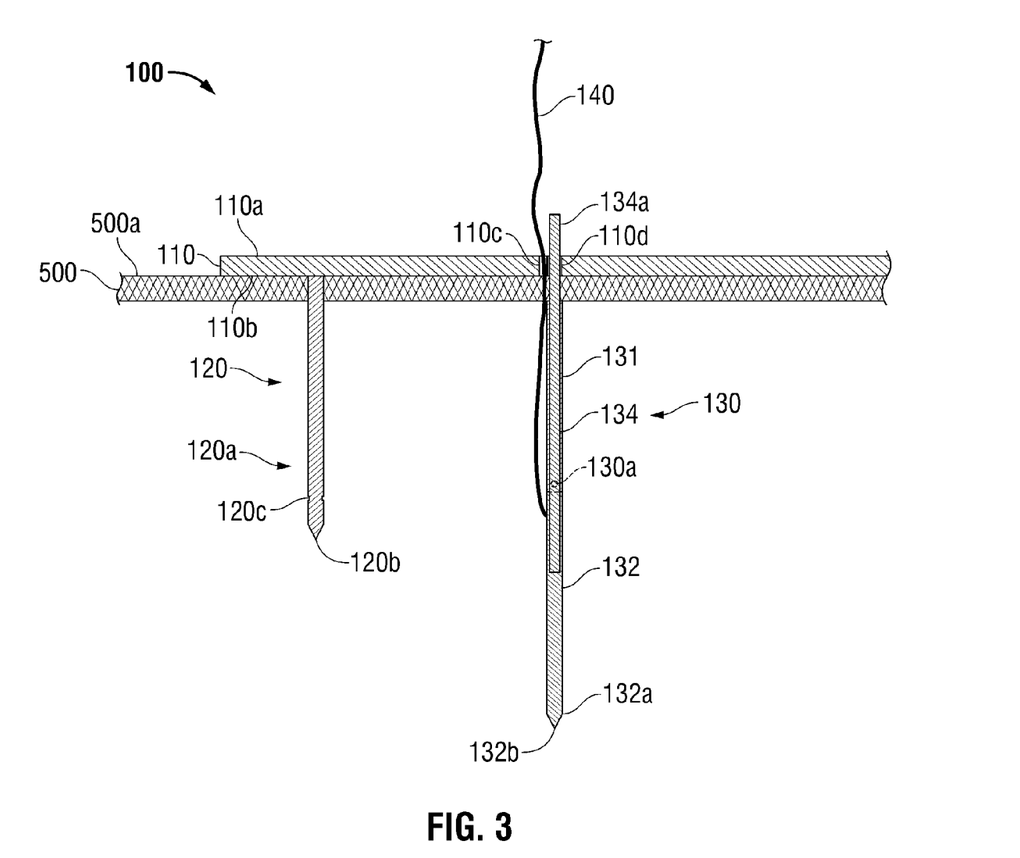
FIG. 3 is a cross-sectional view of the surgical support apparatus as shown in FIG. 2, inserted through the layer of tissue.

Referring to FIG. 3, the surgical support apparatus 100 is shown with the tissue penetrating members 120, 130 inserted into a layer of tissue 500. The platform 110 rests upon body surface 500a. Upon insertion into the layer of tissue 500, the sliding tab 134 is translated proximally, away from second segment 132. Second segment 132 of the second tissue penetrating member 130 is thus free to rotate about the point of attachment 130a to the first segment 131.

Figure 4:
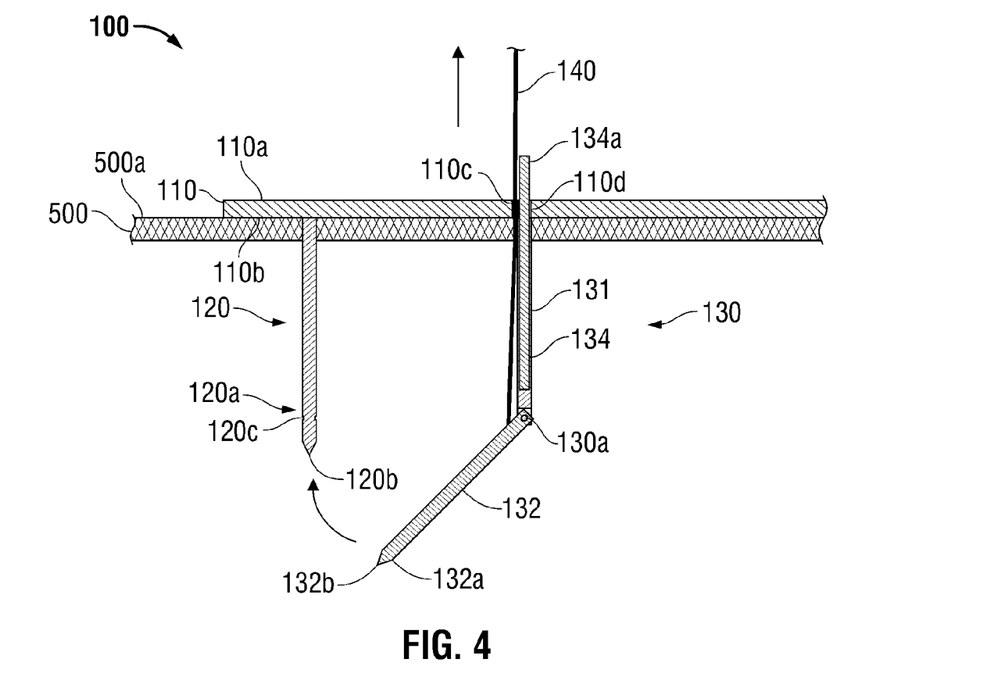
FIG. 4 is a cross-sectional view of the surgical support apparatus as shown in FIG. 3, with the second segment of the second tissue penetrating member being rotated toward the first tissue penetrating member.

Turning now to FIG. 4, the surgical access apparatus 100 is shown with the actuation member 140 engaged and pulled proximally by an operator to rotate the second segment 132 of the tissue penetrating member 130 into position to securely engage the tissue penetrating member 120. As the actuation member 140 is pulled through the aperture 110c and proximally of the platform 110, tensile forces cause the rotation of the second segment 132 about the point of attachment 130a. Second segment 132 of tissue penetrating member 130 radially approaches tissue penetrating member 120 until the engaging surface 132b aligns with and contacts the receiving surface 120c of the tissue penetrating member 120. As discussed above, the tissue penetrating members 120, 130 are urged together by a compressive force.

Figure 5:
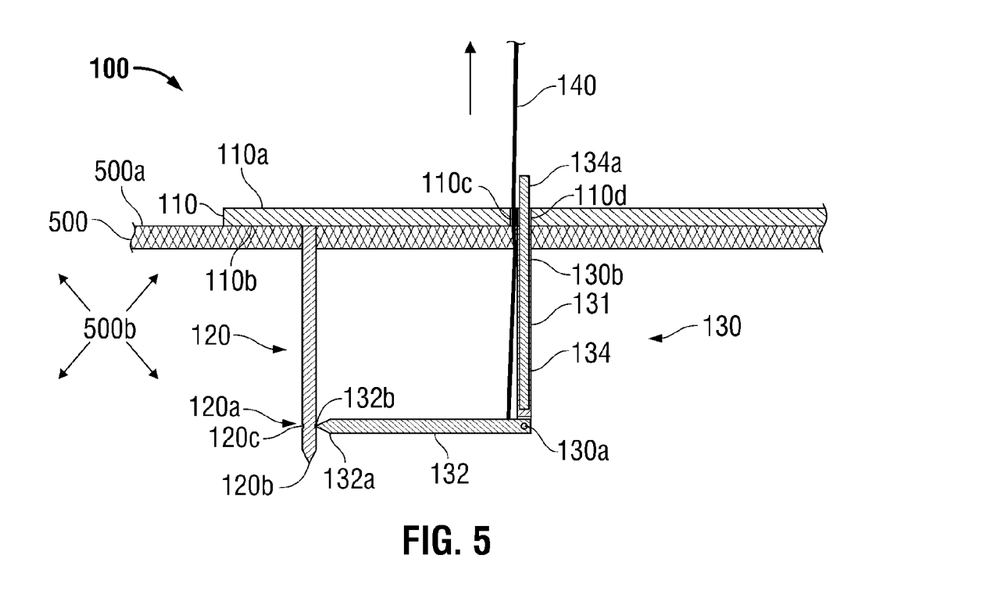
FIG. 5 is a cross-sectional view of the surgical support apparatus as shown in FIG. 3, with the first and second tissue penetrating members securely engaged.

Referring now to FIG. 5, the tissue penetrating members 120, 130 are securely engaged. As shown, the engagement surface 132b is secured with the receiving surface 120c. The engaged tissue penetrating members 120, 130 form a secure structure in internal body cavity 500b. As described earlier, the tissue penetrating members 120, 130 resist disengagement without the intervention of an operator.

In use, an operator will lock first and second segments 131, 132 of tissue penetrating member 130 by translating the sliding tab 134 distally through the passage 130b of tissue penetrating member 130. Tissue penetrating members 120, 130 are then inserted into the layer of tissue 500. Tissue penetrating members 120, 130 may be inserted into the layer of tissue 500 one after another, or simultaneously. The tissue penetrating members 120, 130 are inserted through the layer of tissue 500 until the platform 110 rests upon body surface 500a. Alternatively, the platform 110 may be held securely and suspended above the layer of tissue 500 with the tissue penetrating members 120, 130 inserted to a sufficient depth within internal body cavity 500b.

The operator then grasps the actuation member 140 and exerts a force in the proximal direction. As the actuation member 140 is pulled proximally, the second segment 132 is rotated about the point of attachment 130a and engagement surface 132b radially approaches receiving surface 120c until the surfaces 132b, 120c securely engage via the compressive force generated between tissue penetrating members 120, 130. In other embodiments, the second segment 132 may be rotated about the point of attachment 130a manually or with the use of a tool such as graspers or forceps. With the tissue penetrating members 120, 130 securely engaged, a supportive structure is present in body cavity 500b.

Figure 6:
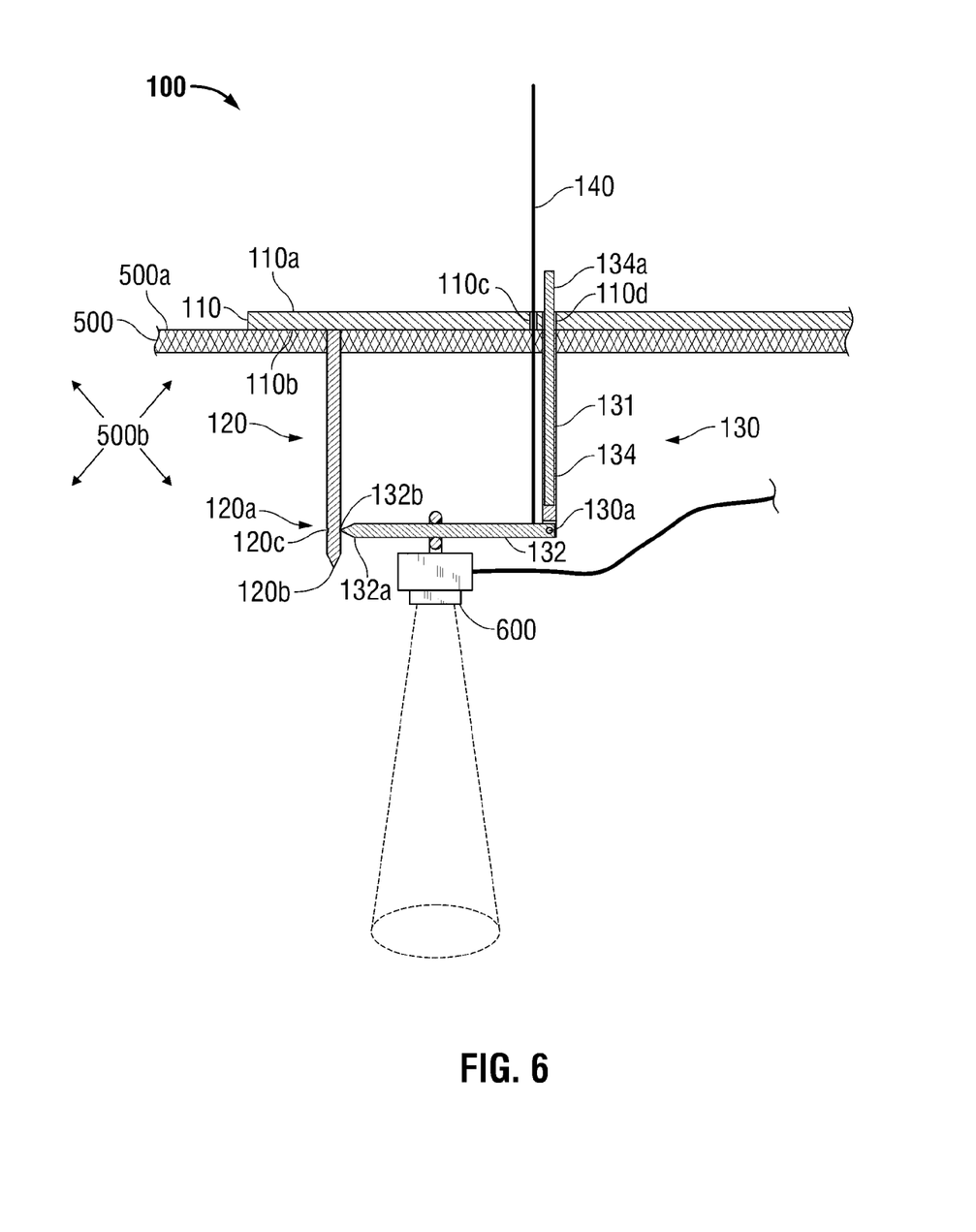
FIG. 6 is a cross-sectional view of the surgical support apparatus as shown in FIG. 5, with a surgical object attached to the second tissue penetrating member.

Referring to FIG. 6, the surgical support apparatus 100 is shown with a surgical object 600 attached to the second segment 132 while the tissue penetrating members 120, 130 are securely engaged. While surgical object 600 is shown here as an imaging element, any number of surgical instruments, tools, or fixtures are contemplated to be attached to surgical support apparatus 100. Additionally, while the surgical object 600 is shown attached to the second segment 132, surgical object 600 may be attached to the first segment 131, tissue penetrating member 120, or any other portion of surgical support apparatus 100. Forces, such as the weight of surgical object 600, exerted distally on the surgical object 600, or a tissue penetrating members 120, 130 are translated to the platform 110, which may rest on body surface 500a and is further attached to an external structure such as a surgical table or support arm (not shown). Thus, surgical objects 600 can be held securely over an internal body cavity 500b, allowing an operator to manipulate surgical instruments or other objects during a minimally invasive procedure.

Figure 7:
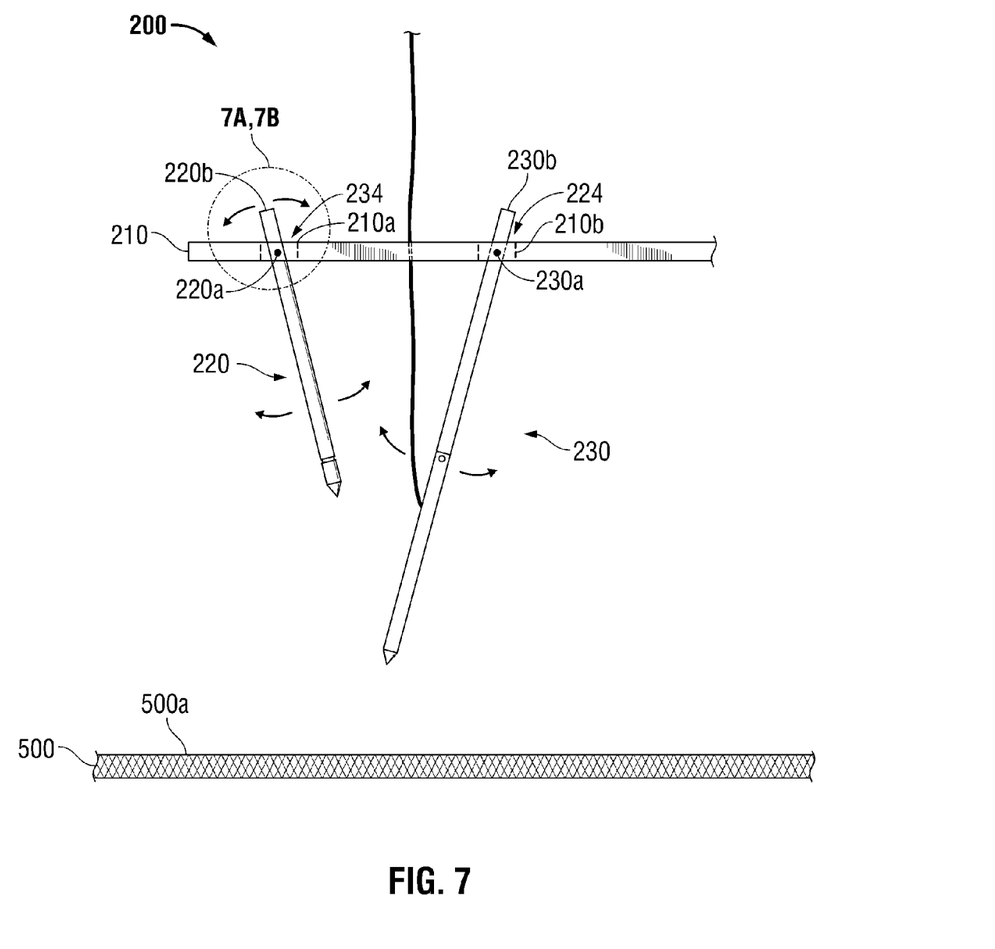
FIG. 7 is a side profile view of an alternative embodiment of a surgical support apparatus, with tissue penetrating members pivotable with respect to a platform, and disposed above a layer of tissue.

Turning now to FIG. 7 an alternative embodiment of a surgical support apparatus, designated 200, is shown in cross-section. Surgical support apparatus 200 includes platform 210. Platform 210 is substantially similar to platform 110, but is not attached to an external member and is configured to rest upon a body surface 500a.

Surgical support apparatus 200 also includes tissue penetrating members 220 and 230. Tissue penetrating members 220 and 230 are substantially similar to tissue penetrating members 120 and 130 as discussed above, but tissue penetrating members 220, 230 are pivotably attached to platform 210 at points of attachment 220a, 230a. Tissue penetrating members 220 and 230 have pivot arms 220b, 230b that extend through apertures 210a, 210b in platform 210 and may be engaged by an operator. Tissue penetrating members 220 and 230 may be pivotably attached to platform 210 with a pin-and-collar configuration as shown, or any other suitable configuration such as a ball-and-socket to allow tissue penetrating members 220, 230 to pivot relative to platform 210 while inhibiting axial translation of the tissue penetrating members 220, 230. Tissue penetrating members 220, 230 incorporate locking mechanisms 224, 234 to maintain tissue penetrating members 220, 230 in a desired orientation relative to platform 210.

Figure 7A:
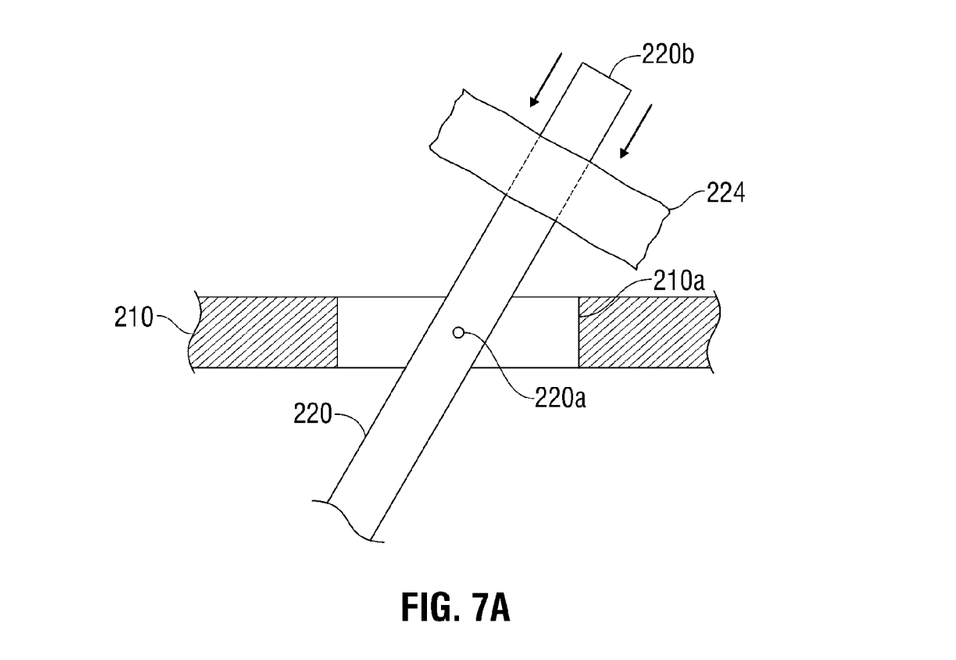
FIG. 7A is an enlarged area of detail view of the area in FIG. 7 showing the tissue penetrating member pivotably mounted to the platform and having a locking mechanism.
Figure 7B:
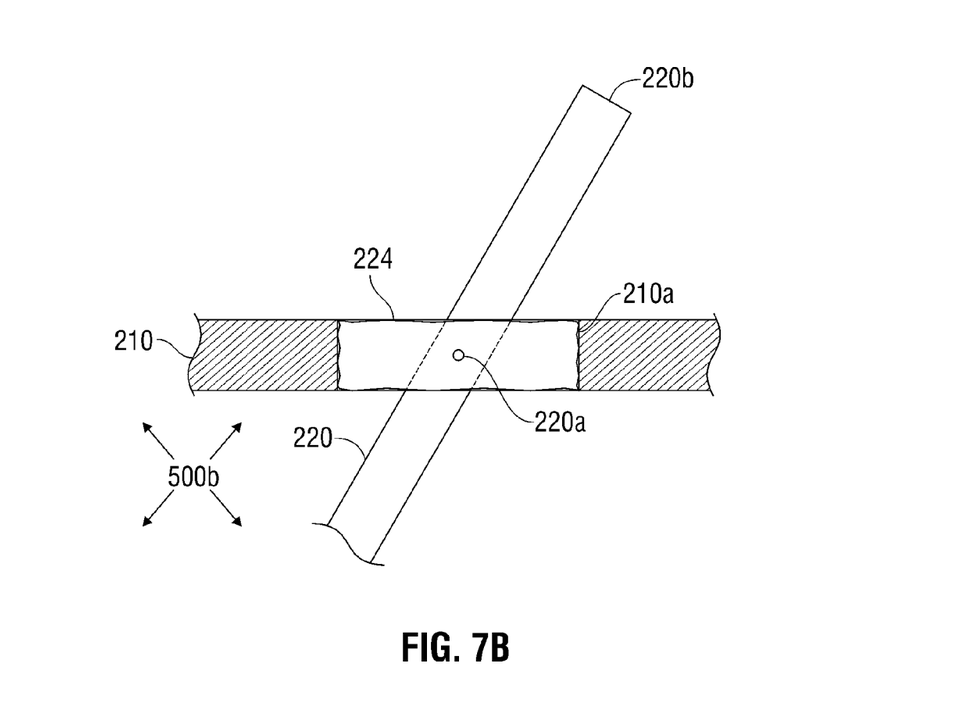
FIG. 7B shows the enlarged area of detail view as shown in FIG. 7A, with the locking mechanism engaged.

Referring now to FIGS. 7A-7B, an enlarged area of detail view around the pivotable attachment of tissue penetrating member 220 to platform 210 is shown. While not shown in FIGS. 7A-7B, the attachment of tissue penetrating member 230 to platform 210 is substantially similar to that of tissue penetrating member 240 and will be discussed concurrently. Turning to FIG. 7A, locking mechanisms 224, 234 are configured as deformable collars disposed around tissue penetrating members 220, 230. Accordingly, locking mechanisms 224, 234 may be formed of a suitable material, such as foam, rubber, gel, or polymer. While shown as an annular collar, locking mechanisms 224, 234 are contemplated to have a variety of shapes and profiles.

Turning to FIG. 7B, locking mechanisms 224, 234 are shown to translate along tissue penetrating members 220, 230. Locking mechanisms 224, 234 may frictionally engage outer surfaces of tissue penetrating members 220, 230 and translate only when the frictional forces between locking mechanisms 224, 234 and tissue penetrating members 220, 230 are overcome by an operator. Locking mechanisms 224, 234 are inserted into apertures 210a, 210b to interfere with the pivotable motion of tissue penetrating members 220, 230 relative to platform 210. The deformable nature of the locking mechanisms 224, 234 allows them to be disposed into apertures 210a, 210b upon forcing by an operator. Locking mechanisms 224, 234 will compactly fill the space defined by apertures 220a, 230a. Locking mechanisms 224, 234 may further deform in apertures 210a, 210b and may lose the form in which they were originally disposed around tissue penetrating members 220, 230 in the course of setting into apertures 210a, 210b. Further, locking mechanisms 224, 234 may be sized differently than apertures 210a, 210b. Locking mechanisms 224, 234 may be pulled proximally out of apertures 220a, 230a to allow pivoting of the tissue penetrating members 220, 230, and may be pressed into apertures 220a, 230a to lock tissue penetrating members 220, 230 into a desired orientation. To this end, platform 220 may include a lever or other structure to remove locking members 224, 234 from apertures 210a, 210b (not shown). In other embodiments, tabs, levers, or any other suitable structures are contemplated as locking mechanisms.

Generally, tissue penetrating members 220, 230 will be locked into an orientation prior to insertion through tissue. However, pivoting of tissue penetrating members 220, 230 may be desirable while they are disposed in a body cavity 500b, such as to close a lateral distance between tissue penetrating members 220, 230 to ensure that a secure engagement may be made between the tissue penetrating members 220, 230 as discussed above with respect to tissue penetrating members 120, 130. Additionally, an operator may pivot tissue penetrating members 220, 230 to disengage tissue penetrating members 220, 230 from each other.

It will be understood that various modifications may be made to the embodiments disclosed herein. Therefore, the above description should not be construed as limiting, but merely as exemplifications of embodiments. Those skilled in the art will envision other modifications within the scope and spirit of the present disclosure.

What is claimed is:

1. A method of assembling a surgical support apparatus in a body cavity, comprising:
   disposing a surgical support apparatus over a body cavity, the surgical support apparatus having:
   an elongate member;
   a first tissue penetrating member attached to the elongate member; and
   a second tissue penetrating member attached to the elongate member, the second tissue penetrating member having first and second segments;
   cutting through a tissue layer with the first and second tissue penetrating members to access the body cavity;
   manipulating the tissue penetrating members of the surgical support apparatus to form a supportive structure in the body cavity; and
   attaching surgical objects to the supportive structure.

2. The method of claim 1, wherein the first and second segments are hingably attached, a portion of the second segment configured and dimensioned to engage a portion of the first tissue penetrating member.

3. The method of claim 2, wherein the surgical support apparatus defines a first state when the first and second segments of the second tissue penetrating member are disposed in a substantially straight condition and defines a second state when the second segment of the second tissue penetrating member is attached to a portion of the first tissue penetrating member.

4. The method of claim 3, further including transitioning the surgical support apparatus from the first state to the second state.

5. The method of claim 2, further including maintaining the first segment in an orientation relative to the second segment with a locking mechanism of the surgical support apparatus.

6. The method of claim 1, wherein at least one of the first and second tissue penetrating members is pivotable relative to the elongate member and the method further includes locking at least one of the first and second tissue penetrating members in an orientation relative to the elongate member.

7. The method of claim 1, wherein manipulating the surgical support apparatus includes forming the surgical support apparatus with the tissue layer between the supportive structure and the elongate member.

8. The method of claim 1, wherein attaching the surgical objects to the supportive structure includes attaching the surgical objects to the supportive structure with the tissue layer between the supportive structure and the elongate member.

9. A method of assembling a surgical support apparatus in a body cavity, comprising:
    disposing a surgical support apparatus over a body cavity, the surgical support apparatus having:
        an elongate member;
        a first tissue penetrating member extending from the elongate member; and
        a second tissue penetrating member extending from the elongate member, the second tissue penetrating member having first and second segments;
    using the first and second tissue penetrating members to create openings through a tissue layer for accessing the body cavity with the first and second tissue penetrating members;
    manipulating the tissue penetrating members of the surgical support apparatus to form a supportive structure in the body cavity; and
    attaching a surgical object to the supportive structure.

10. The method of claim 9, wherein manipulating the tissue penetrating members includes engaging a portion of the first tissue penetrating member with a portion of the second segment of the second tissue penetrating member.

11. The method of claim 10, wherein manipulating the tissue penetrating members includes transitioning the surgical support apparatus from a first state, wherein the first and second segments of the second tissue penetrating member are disposed in a linear orientation, to a second state, wherein the second segment of the second tissue penetrating member is in contact with a portion of the first tissue penetrating member.

12. The method of claim 10, further comprising maintaining the first segment in an orientation relative to the second segment using a locking mechanism of the surgical support apparatus.

13. The method of claim 9, further comprising locking at least one of the first and second tissue penetrating members in an orientation relative to the elongate member, wherein at least one of the first and second tissue penetrating members is pivotable relative to the elongate member.

14. The method of claim 9, wherein manipulating the surgical support apparatus includes forming the surgical support apparatus with the tissue layer between the supportive structure and the elongate member.

15. The method of claim 9, wherein attaching the surgical object to the supportive structure includes attaching the surgical object to the supportive structure with the tissue layer between the supportive structure and the elongate member.

16. The method of claim 9, wherein using the first and second tissue penetrating members to create openings through a tissue layer includes maintaining the second tissue penetrating member in a straight configuration with a sliding tab slidably disposed over a portion of the first and second segments.

* * * * *